US009539145B2

(12) United States Patent
Vetek et al.

(10) Patent No.: US 9,539,145 B2
(45) Date of Patent: Jan. 10, 2017

(54) METHODS AND APPARATUS FOR REPRESENTING USER OUTPUT DATA BY TRANSCUTANEOUS STIMULATION OF A USER'S OPTIC NERVE

(75) Inventors: Akos Vetek, Helsinki (FI); Jari Kangas, Tampere (FI); Leo Karkkainen, Helsinki (FI); Tatiana G. Evreinova, Tampere (FI); Grigori E. Evreinov, Tampere (FI)

(73) Assignee: Nokia Technologies Oy, Espoo (FI)

( * ) Notice: Subject to any disclaimer, the term of this patent is extended or adjusted under 35 U.S.C. 154(b) by 760 days.

(21) Appl. No.: 13/370,720

(22) Filed: Feb. 10, 2012

(65) Prior Publication Data

US 2013/0211475 A1    Aug. 15, 2013

(51) Int. Cl.
| A61N 1/36 | (2006.01) |
| A61F 9/08 | (2006.01) |
| A61N 1/372 | (2006.01) |
| A61N 1/04 | (2006.01) |

(52) U.S. Cl.
CPC ............... *A61F 9/08* (2013.01); *A61N 1/0456* (2013.01); *A61N 1/36014* (2013.01); *A61N 1/37258* (2013.01); *A61N 1/36046* (2013.01)

(58) Field of Classification Search
USPC ............................... 607/53, 54, 139; 600/383
See application file for complete search history.

(56) References Cited

U.S. PATENT DOCUMENTS

| 4,305,402 | A | * | 12/1981 | Katims | 600/554 |
| 4,664,117 | A | * | 5/1987 | Beck | 607/54 |
| 4,979,508 | A | | 12/1990 | Beck | 128/419 R |
| 5,036,850 | A | * | 8/1991 | Owens | 607/66 |
| 5,674,263 | A | * | 10/1997 | Yamamoto et al. | 607/54 |
| 6,442,431 | B1 | * | 8/2002 | Veraart et al. | 607/54 |
| 6,549,808 | B1 | | 4/2003 | Gisel et al. | 607/53 |
| 6,684,107 | B1 | * | 1/2004 | Binder | 607/72 |
| 8,068,644 | B2 | * | 11/2011 | Tkacik | 382/114 |
| 2006/0058857 | A1 | | 3/2006 | Tano et al. | 607/54 |
| 2006/0241753 | A1 | | 10/2006 | Suaning et al. | 623/6.63 |
| 2009/0156886 | A1 | | 6/2009 | Burgio et al. | 600/27 |
| 2011/0166624 | A1 | | 7/2011 | Dietrich et al. | |

FOREIGN PATENT DOCUMENTS

| DE | 102008024972 A1 | 12/2009 |
| EP | 0743051 A2 | 11/1996 |

OTHER PUBLICATIONS

"Brain Stimulation Therapies—Stimulation to modulate brain activity", Edmonton Neurotherapy, 13 pgs.

(Continued)

*Primary Examiner* — Eugene T Wu
(74) *Attorney, Agent, or Firm* — Harrington & Smith

(57) ABSTRACT

Systems and techniques for providing data to a user in the form of perceived light signals caused by transcutaneous stimulation of the user's optic nerve. User output data, suitably representing data collected, generated, or processed by a data processing device, is used to generate user output data. The user output data is converted to representations corresponding to light signals, and control functions are performed to cause generation of electrical impulses which, when applied to the skin of a user, stimulate the optic nerve of the user so as to cause the user to perceive the light signals.

20 Claims, 3 Drawing Sheets

(56) References Cited

OTHER PUBLICATIONS

"A Vision System for Providing 3D Perception of the Environment via Transcutaneous Electro-Neural Stimulation", Simon Meers, et al., School of IT and Computer Science, Univeristy of Wollongong, Jul. 14-16, 2004, pp. 546-552.
"A Model of Safe Levels for Electrical Stimulation", Robert V. Shannon, IEEE Transactions on Biomedical Engineering, vol. 39, No. 4, Apr. 1992, pp. 424-426.

* cited by examiner

METHODS AND APPARATUS FOR REPRESENTING USER OUTPUT DATA BY TRANSCUTANEOUS STIMULATION OF A USER'S OPTIC NERVE

TECHNICAL FIELD

The exemplary and non-limiting embodiments of this invention relate generally to human-machine interfaces, and more specifically relate to mechanisms for transcutaneous stimulation of the optic nerve to produce visual responses.

BACKGROUND

Present day electronic devices process and generate substantial amounts of data, and are able to deliver data generated by the devices themselves as well as data sensed and processed by the devices. Data is typically delivered to users in the form of visual displays, and is also frequently delivered audibly. Visual displays are naturally of little value to visually impaired users, particularly users who are severely visually impaired, and audible displays are similarly of little value to hearing-impaired users. In addition, displays of electronic devices must frequently compete with many other visual and audible stimuli, even for users with normal sight and hearing. Considerable efforts have been made to provide visual information to visually impaired persons, and it is easy to understand how the lives of such persons might be improved by technology that could let them see the world around them. Devices that stimulate the visual cortex and the optic nerve typically involve implants or other invasive techniques.

SUMMARY

In one embodiment of the invention, an apparatus comprises memory, at least one processor, and a program of instructions. The program of instructions is configured to, with the memory and the at least one processor, configure the apparatus to perform actions comprising at least generating user output data, converting the user output data to representations corresponding to light signals, and performing control functions to cause generation of electrical outputs. The electrical outputs, when applied to the skin of a user, stimulate an optic nerve of the user so as to cause the user to perceive the light signals.

In another embodiment of the invention, a method comprises generating user output data, converting the user output data to representations corresponding to light signals, and performing control functions to cause generation of electrical outputs. When applied to the skin of a user, the electrical outputs stimulate an optic nerve of the user so as to cause the user to perceive the light signals.

In another embodiment of the invention, a computer readable medium stores a program of instructions. When executed by a processor, the program of instructions configures an apparatus to perform actions comprising at least generating user output data, converting the user output data to representations corresponding to light signals, and performing control functions to cause generation of electrical outputs. When applied to the skin of a user, the electrical outputs stimulate an optic nerve of the user so as to cause the user to perceive the light signals.

These and other embodiments and aspects are detailed below with particularity.

DETAILED DESCRIPTION

Embodiments of the present invention recognize that stimulation of the optic nerve through invasive techniques such as surgery is more or less traumatic to a subject and obviously limits its applicability to persons with severe visual impairments, such that the benefit provided by stimulation visual centers would overcome the trauma of placing devices in the body. In addition, various embodiments of the invention recognize that noninvasive techniques of stimulating the optic nerve naturally reduce the negative impact on the patient and thus make optic nerve stimulation acceptable in situations less grave than serious visual impairment. Embodiments of the present invention also recognize that many mechanisms to stimulate the optic nerve or other visual centers are cumbersome and limit the mobility of the user.

Embodiments of the present invention therefore provide a portable, or completely self-contained, device that converts data to electrical impulses that can be applied to the skin of a patient to stimulate the optic nerve. Such stimulation can cause the perception of light by a user, and different signals causing different levels and durations of stimuli can cause perception of different light patterns. A user device, such as a computer or mobile device may produce a signal that can be converted to electrical stimuli, and signals produced by the user device may thus be converted to visual patterns that can be perceived by the user even in the face of visual impairments. Alternatively, even for users having normal vision, the signals may be provided to a user in ways that can be perceived even in the face of the visual and auditory clutter that frequently surrounds users in their daily activities.

Figure 1:
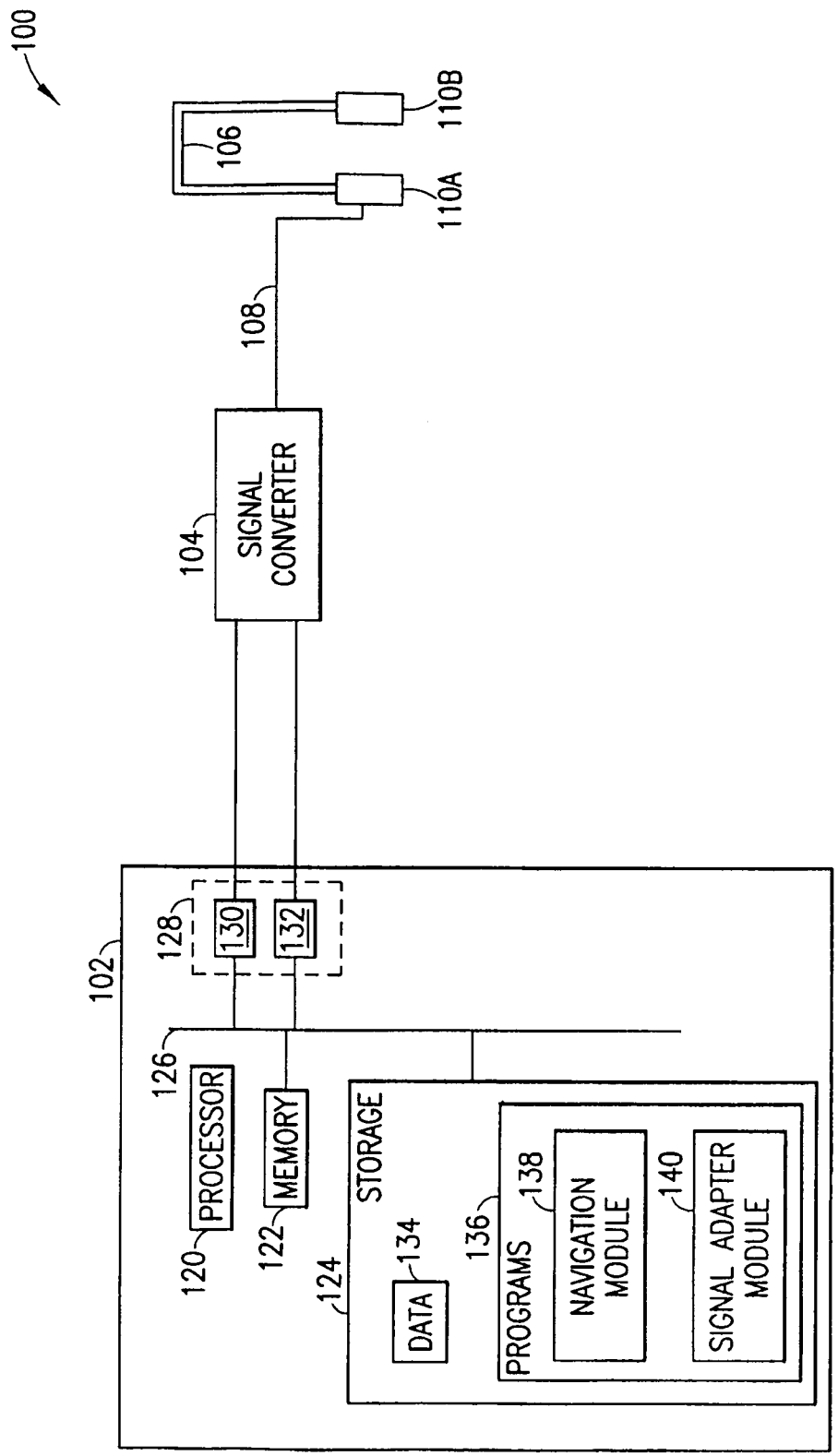
FIG. 1 illustrates a system according to an embodiment of the present invention.

FIG. 1 illustrates a system 100 according to an embodiment of the present invention. The system 100 comprises a data processing device 102, which may be a computer, portable data processing device, or other device capable of processing or detecting data and delivering information through a user interface. The system 100 further comprises a signal converter 104, which receives signals from the data processing device 102 and converts the signals to electrical impulses that be applied to a user's skin and produce transcutaneous stimulation of the optic nerve of a user. The system 100 additionally comprises a contact interface 106, that may be worn by a user. The contact interface 106 comprises a connector 108 providing a connection to the signal converter 104, as well as contacts 110A and 110B that can carry electrical impulses to the skin of a user. The electrical impulses produce visual perceptions on the part of the user, with the visual perceptions varying based on variations of the signal produced by the data processing device 102.

The data processing device 102 comprises a processor 120, memory 122, and storage 124, communicating over a bus 126. The data processing device 102 further comprises a signal interface 128, which in one or more embodiments of the invention may comprise an audio port 130 and a video port 132. The signal converter may suitably connect to one or more of the audio port 130 and the video port 132, converting received signals from the connected port or ports to electrical impulses that can be applied by the contact interface 106.

The data processing device 102 employs data 134 and programs 136, suitably residing in storage 124. The data processing device 102 may include various software modules used in its normal operation. One example of such a module, and one useful for illustrating embodiments of the present invention, is a navigation module 138. The navigation module 138 supports various maps and other devices for informing a user of his or her location or guiding the user to a desired location. One mechanism particularly useful for illustrated the present invention is navigation to a waypoint. The navigation module 138 may receive inputs to set a waypoint and then may provide navigation signals to inform the user if he or she is following a correct path to the waypoint. In many navigation aids, a user is pointed with a directional indicator that points right or left if the user has deviated from the path to the left or the right, respectively. Such a mechanism is easily adapted to embodiments of the present invention. It will be noted that the contact interface 106 comprises contacts 110A and 110B. The contact interface 106 can therefore stimulate the user with either the contact 110A or the contact 110B, as needed. The data processing device 102 may therefore employ a signal adapter module 140, to analyze information to be provided to a user by various software modules and adapt the information to a form that can be readily interpreted by the user when providing through transcutaneous stimulation using embodiments of the present invention. In the case of a directional indication to a waypoint, the signal adapter module 140 may adapt directional indications generated by the navigation module 138 so that a directional arrow pointing left will be represented by a stimulation on the left contact, which may be here 110A, and a directional arrow pointing right will be represented by a stimulation on the right contact, which may be here 110B. The stimulation at 110A will cause the user to perceive a light to the left, and the stimulation at 110B will cause the user to perceive a light to the right. As the user deviates from the path to the right, the navigation module 138 may produce a left-pointing directional arrow that also indicates the degree of deviation, and the signal adapter module 140 may interpret the directional arrow and produce, based on the interpretation, a pulse at the left contact 110, with a pulse frequency that increases with increasing deviation and slows with decreasing deviation, with the pulse ceasing when the user is following the correct path. The pulse may, for example, be produced in the form of a stereo audio signal characterized by a pulsed tone on the left or right audio channel of the signal, delivered through the audio port 130 and received by the signal converter 104. The signal converter 104 converts the audio signal to electrical pulses to be delivered to the contact interface 106, as described in greater detail below.

Figure 2:
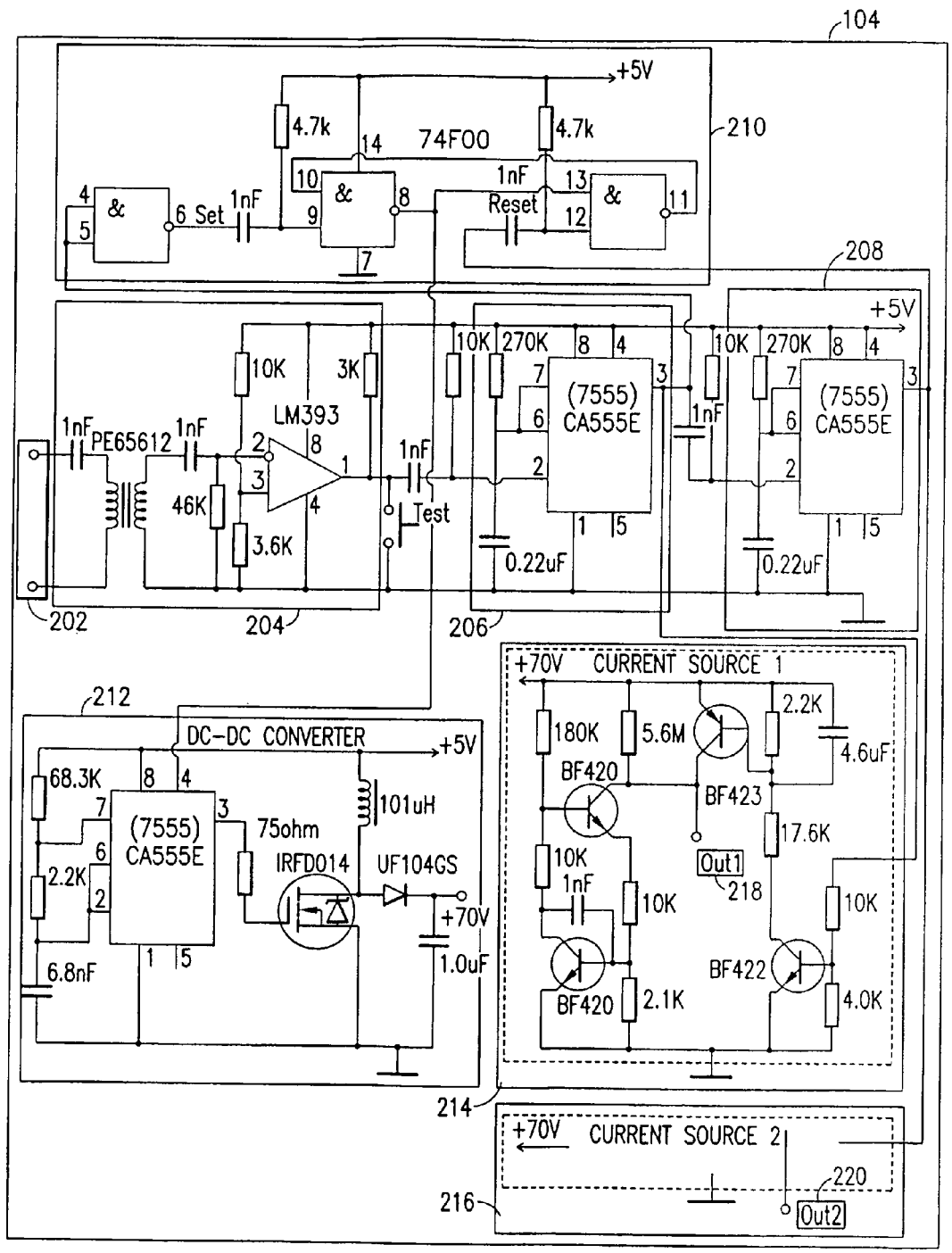
FIG. 2 illustrates a signal converter according an embodiment of the present invention.

FIG. 2 illustrates additional details of the signal converter 104. In the present exemplary embodiment, the signal converter 104 comprises an input interface 202, providing an input to a voltage comparator 204. The output of the voltage comparator 204 is supplied to a first timer 206, whose output is supplied to a second timer 208. The output of the first timer 206 is also supplied to a trigger 210, as is the output of the second timer 208. The output of the trigger 210 is supplied to a voltage boost converter 212. The timers 206 and 208 also control current sources 214 and 216, which supply first and second output ports 218 and 220. The first and second outputs 218 and 220 supply voltage to the contacts 110A and 110B of the contact interface 106.

When a signal is applied to the input 202 of the signal converter 104, the signal drives the comparator 204. The comparator 204 produces an output based on the signal supplied to the input 202. The timer 206 is switched on by a rising negative edge of the comparator 204. The rising positive edge of the timer 206 sets the trigger 210 to an active state, to switch on the voltage boost converter 212. The timer 206 switches on the current source 214, and generates a pulse of positive polarity at the output port 218 of the current source 214.

The falling negative edge of the timer 206 switches on the timer 208. The timer 208 switches on the current source 216, and generates a pulse of negative polarity at the output port 220 of the current source 216. The falling edge of the timer 208 resets the trigger 210 to an inactive state for switching off the voltage boost converter 212. Therefore the voltage boost converter 212 operates only during transcutaneous electrical stimulation. The current sources 214 and 216 combine to produce a balanced differential signal between the outputs ports 218 and 220, loaded by the skin of a user, as the signal is delivered to the user through the contact interface 106.

Suitable signal durations and other parameters may suitably comprise 80 ms pulses, with currents within the limits of 240±20 μA, with a load impedance ranging within the limits of 5-300 kohm. In one embodiment, the signals may be produced by the data processing device 102 in the form of bursts of pulses with a time between pulses of 5, 10, and 15 ms, and a signal duration of 165, 170, and 175 ms. Such signal durations will produce weak, mild, or strong sensations of a flickering bright spot, respectively.

Figure 3:
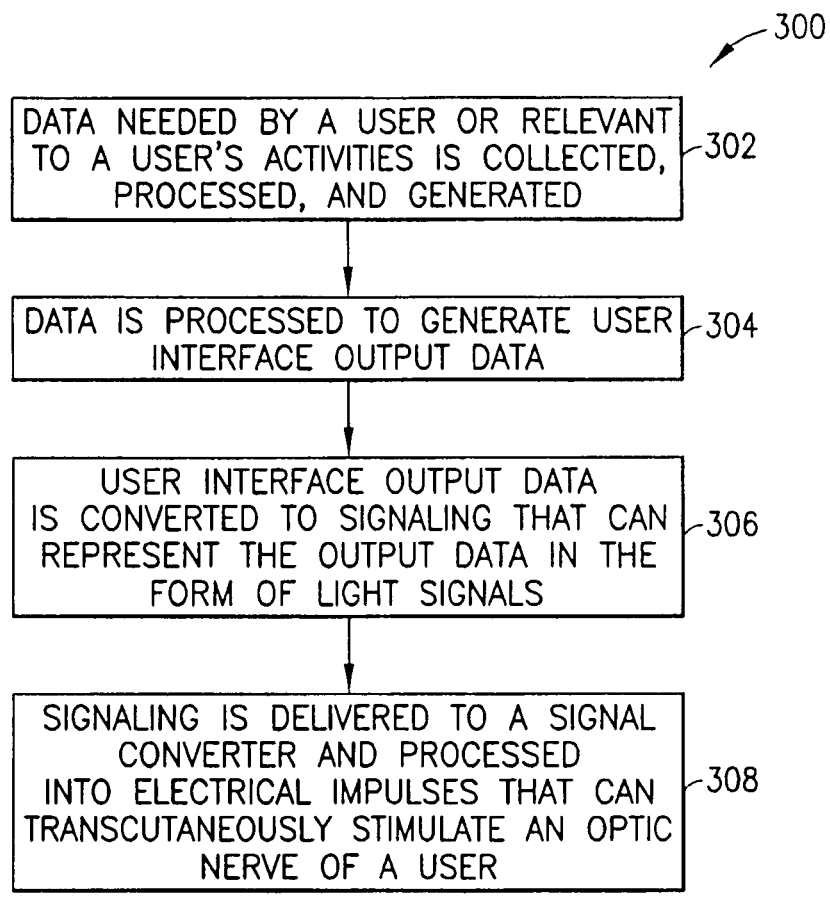
FIG. 3 illustrates a process according to an embodiment of the present invention.

FIG. 3 illustrates a process 300 according to an embodiment of the present invention. At step 302, data needed by a user or relevant to a user's activities is collected, processed and generated, suitably by a data processing device. The data may comprise data from any number of sources or related to any number of events or phenomena. Examples of such events of phenomena include, for example, alerts generated by the data processing device, such as calendar alerts, incoming communication alerts, or the like. Other examples include environmental conditions, such as obstacles or hazards, and routing directions. At step 304, appropriate data is processed to generate user interface output data. The user interface output data may be typical of data generated by typical user interface devices, such as display indications, audio signals, or the like. At step 306, the user interface output data is converted to signaling representing the output data, with the conversion being performed in such a way that signaling in the form of light signals can comprehensibly represent the interface output data. At step 308, the signaling is delivered to a signal converter and processed into electrical impulses that can transcutaneously stimulate an optic nerve of the user.

While various exemplary embodiments have been described above it should be appreciated that the practice of the invention is not limited to the exemplary embodiments shown and discussed here. Various modifications and adaptations to the foregoing exemplary embodiments of this invention may become apparent to those skilled in the relevant arts in view of the foregoing description.

Further, some of the various features of the above non-limiting embodiments may be used to advantage without the corresponding use of other described features.

The foregoing description should therefore be considered as merely illustrative of the principles, teachings and exemplary embodiments of this invention, and not in limitation thereof.

We claim:

1. A method comprising:
   generating user output data;

converting the user output data to representations corresponding to light signals; and performing control functions to at least two current sources to cause generation of electrical outputs in the form of at least a balanced differential signal which, when applied to the skin of a user, stimulate an optic nerve of the user so as to cause the user to perceive the light signals.

2. The method of claim 1, further comprising generating the electrical outputs in the form of electrical pulses, and the electrical pulses are generated based on one or more electrical signals representing the user output data.

3. The method of claim 2, wherein the one or more electrical signals comprise an analog audio signal representing audible pulses.

4. The method of claim 2, wherein the signal converter generates left electrical pulses to stimulate the left optic nerve of the user and right electrical impulses to stimulate the right optic nerve of the user.

5. The method of claim 2, wherein converting the user output data to representations corresponding to light signals comprises generating representations corresponding to light pulses of intensities based at least in part on the user output data.

6. The method of claim 2, wherein converting the user output data to representations corresponding to light signals comprises generating representations corresponding to light pulses of durations varying based at least in part on the user output data.

7. The method of claim 2, wherein converting the user output data to representations corresponding to light signals comprises generating representations corresponding to light pulses on one side of the user or the other based on the output data.

8. An apparatus comprising:
at least one processor;
memory storing a program of instructions;
wherein the program of instructions is configured to, with the at least one processor, cause the apparatus to perform actions comprising at least:
generating user output data;
converting the user output data to representations corresponding to light signals; and
performing control functions to at least two current sources to cause generation of electrical outputs in the form of at least a balanced differential signal which, when applied to the skin of a user, stimulate an optic nerve of the user so as to cause the user to perceive the light signals.

9. The apparatus of claim 8, further comprising a signal converter to generate the electrical outputs in the form of electrical pulses, and wherein the signal converter generates the electrical pulses based on one or more electrical signals representing the user output data.

10. The apparatus of claim 9, wherein the one or more electrical signals comprise an analog audio signal representing audible pulses.

11. The apparatus of claim 9, wherein the signal converter generates left electrical pulses to stimulate the left optic nerve of the user and right electrical impulses to stimulate the right optic nerve of the user.

12. The apparatus of claim 9, wherein converting the user output data to representations corresponding to light signals comprises generating representations corresponding to light pulses of intensities based at least in part on the user output data.

13. The apparatus of claim 9, wherein converting the user output data to representations corresponding to light signals comprises generating representations corresponding to light pulses of durations varying based at least in part on the user output data.

14. The apparatus of claim 9, wherein converting the user output data to representations corresponding to light signals comprises generating representations corresponding to light pulses on one side of the user or the other based on the output data.

15. A non-transitory computer readable medium storing a program of instructions, execution of which by a processor configures an apparatus to perform actions comprising at least:
generating user output data;
converting the user output data to representations corresponding to light signals; and
performing control functions to at least two current sources to cause generation of electrical outputs in the form of at least a balanced differential signal which, when applied to the skin of a user, stimulate an optic nerve of the user so as to cause the user to perceive the light signals.

16. The computer readable medium of claim 15, wherein the apparatus is further configured to generate the electrical outputs in the form of electrical pulses, and the electrical pulses are generated based at least in part on one or more electrical signals representing the user output data.

17. The computer readable medium of claim 16, wherein the one or more electrical signals comprise an analog audio signal representing audible pulses.

18. The computer readable medium of claim 16, wherein the signal converter generates left electrical pulses to stimulate the left optic nerve of the user and right electrical impulses to stimulate the right optic nerve of the user.

19. The computer readable medium of claim 16, wherein converting the user output data to representations corresponding to light signals comprises generating representations corresponding to light pulses of intensities based at least in part on the user output data.

20. The computer readable medium of claim 16, wherein converting the user output data to representations corresponding to light signals comprises generating representations corresponding to light pulses of durations varying based at least in part on the user output data.

* * * * *